US00PP22407P3

(12) United States Plant Patent
de Jong

(10) Patent No.: US PP22,407 P3
(45) Date of Patent: Dec. 27, 2011

(54) CYPRESS TREE NAMED 'GREEN ROCKET'

(50) Latin Name: *Cupressocyparis leylandii*
Varietal Denomination: Green Rocket

(75) Inventor: Cornelis Henricus Maria de Jong, Biezenmortel (NL)

(73) Assignee: Van Vliet New Plants BV, Stroe (NL)

( * ) Notice: Subject to any disclaimer, the term of this patent is extended or adjusted under 35 U.S.C. 154(b) by 0 days.

(21) Appl. No.: 12/660,379

(22) Filed: Feb. 25, 2010

(65) Prior Publication Data

US 2011/0209258 P1 Aug. 25, 2011

(51) Int. Cl.
*A01H 7/00* (2006.01)

(52) U.S. Cl. ..... Plt./213

(58) Field of Classification Search ..... Plt./213
See application file for complete search history.

(56) References Cited

OTHER PUBLICATIONS

Upov-rom GTITM Plant Variety Database 2010-06 GTI Jouve Retrieval Software. Citation for *Cupressocyparis* 'Green Rocket', one page.*
Trademark Electronic Search System (TESS), retrieved on Feb. 24, 2011, citation for Green Rocket, 2 pp.*

* cited by examiner

*Primary Examiner* — June Hwu
(74) *Attorney, Agent, or Firm* — Jondle & Associates, P.C.

(57) ABSTRACT

'Greenpower ' is a new *Cupressocyparis leylandii* variety particularly distinguished by having a sturdy, straight upright leader, which creates the cultural advantage of not being necessary to tie the leader to a cane in order to maintain a good upright growth, a very narrow, pyramidal growth habit, and dark green foliage is disclosed.

2 Drawing Sheets

Genus and species: *Cupressocyparis leylandii.*
Variety denomination: 'Greenpower'.

BACKGROUND OF THE NEW TREE

The present invention relates to a new and distinct variety of *Cupressocyparis leylandii* plant and is hereinafter referred to by the variety name 'Greenpower'. 'Greenpower' is a naturally-occurring branch mutation of an un-named selection of *Cupressocyparis leylandii* (unpatented) discovered in a cultivated nursery in Biezenmortel, The Netherlands in 2003. The nursery has a dilluvial sandy soil with a pH of 6.7 and an annual rainfall of approximately 670 mm. The location can be rated as USDA Zone 8a.

'Greenpower' has been asexually reproduced for five generations by softwood cuttings in a controlled environment in Biezenmortel, The Netherlands since 2005. 'Greenpower' has been found to retain its distinctive characteristics through successive generations of asexual propagation via softwood cuttings.

REFERENCE TO PLANT BREEDERS' RIGHTS

Plant Breeders' Rights for this variety were filed in the European Union on Nov. 10, 2008.

SUMMARY OF THE INVENTION

The following characteristics of the new variety have been repeatedly observed and can be used to distinguish 'Greenpower' as a new and distinct variety of *Cupressocyparis leylandii* plant:

1. A sturdy, straight upright leader which creates the cultural advantage of not being necessary to tie the leader to a cane in order to maintain a good upright growth;

2. Very narrow, upright growth habit, and narrow, conical plant shape; and
3. Dark green foliage.

DESCRIPTION OF THE PHOTOGRAPHS

This new *Cupressocyparis leylandii* plant is illustrated by the accompanying photographs which show the tree's form and foliage. The colors shown are as true as can be reasonably obtained by conventional photographic procedures. Photographs were taken of a 3-year-old tree in October 2009.

DESCRIPTION OF THE NEW TREE

Figure 1:
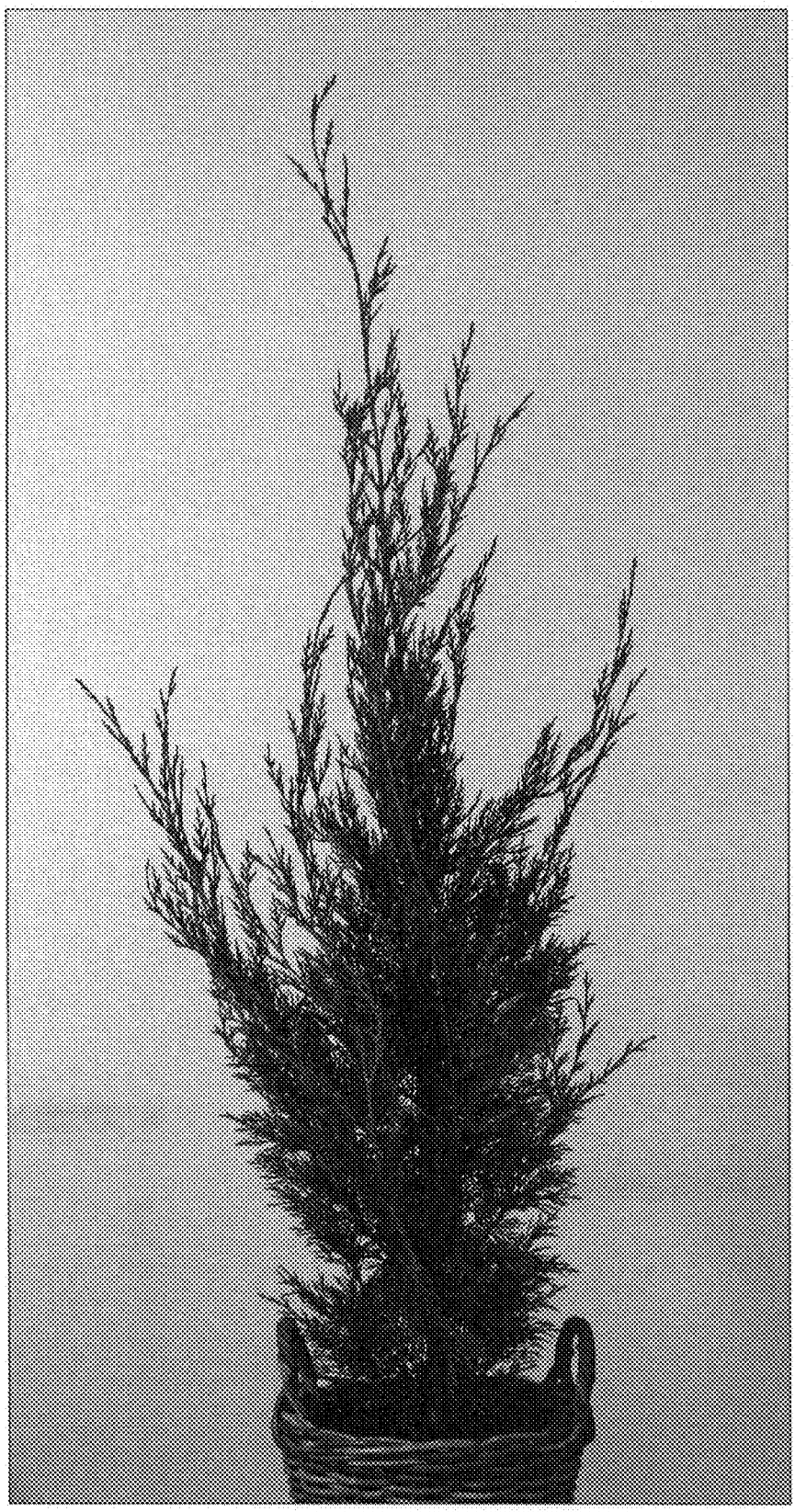
FIG. 1 shows the overall plant habit.
Figure 2:
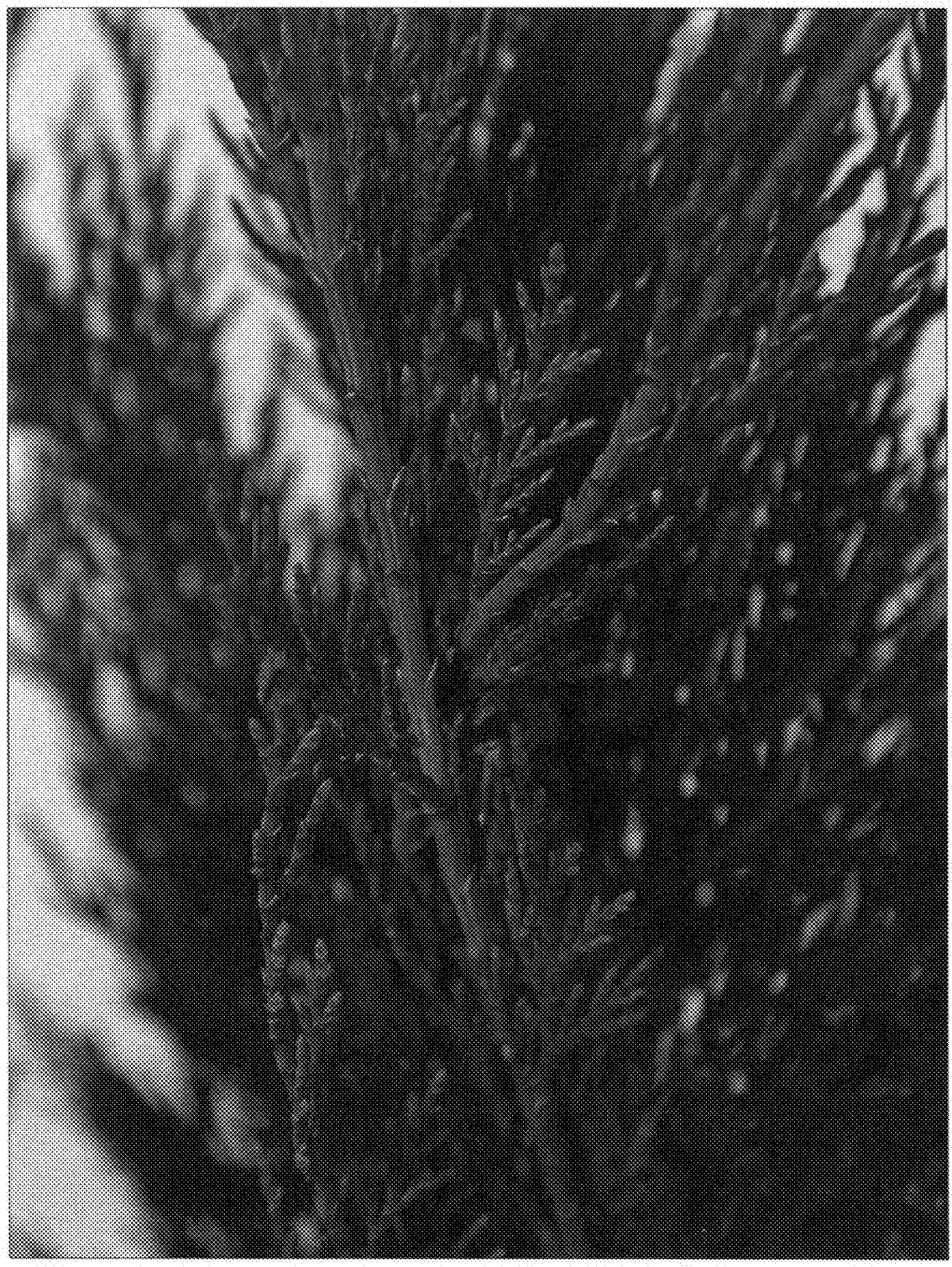
FIG. 2 shows a close-up of the leaves.

In the following description, color references are made to The Royal Horticultural Society Colour Chart, fifth edition, 2007. The following detailed description sets forth the distinctive characteristics of 'Greenpower'. The data which define these characteristics were collected from asexual reproductions carried out in Biezenmortel, The Netherlands in October 2009. The detailed description was taken from 3-year-old trees grown outdoors under normal outdoor light. Daytime temperatures ranged from 12° C. to 28° C., while night time temperatures ranged from 4° C. to 16° C. No growth retardants were used.

DETAILED BOTANICAL DESCRIPTION OF THE NEW TREE

Classification:

*Botanical name.*—*Cupressocyparis leylandii.*
*Common name.*—Leyland Cypress.
*Denomination.*—'Greenpower'.

Parentage:

*Parent.*—Naturally-occurring branch mutation of *Cupressocyparis leylandii* (unpatented).

Tree:

*Type.*—Woody perennial, shrub, conifer or evergreen.

*Propagation type.*—Softwood.

*Shape.*—Narrow conical.

*Growth habit.*—Narrow upright, pyramidal.

*Growth rate.*—Average, approximately 40.0 cm per season for a young plant.

*Time to initiate roots* (*average*).—In summer, 20 weeks with an average soil/air temperature of 20° C.

*Time to produce a finished plant.*—Approximately 1 year.

*Roots.*—Density: Moderate. Branching: Low to moderate. Color: RHS N167D (Greyed-orange). Thickness: Medium. Texture: Moderately fibrous.

*Size.*—Height: 137.8 cm. Width (spread): 52.9 cm.

*Vigor.*—Moderate.

*Trunk.*—Surface texture: Young tree: Smooth. Mature tree: Shallowly ridged and flaking. Color: From RHS 175A (Greyed-orange) and RHS 176A (Greyed-orange) to RHS 200C (Brown).

Lateral branches:

*Branching habit.*—Moderate; no basal branching.

*Number of lateral branches per plant* (*average*).—43.

*Appearance of lateral branches.*—Rounded, covered with scale-like leaves, dull.

*Color.*—Young branch: From RHS 143A (Green) to RHS 144A (Yellow-green). Mature branch: From RHS 175A (Greyed-orange) and RHS 176A (Greyed-orange) to RHS 200C (Brown).

*Diameter* (*average*).—0.35 cm.

*Length* (*average*).—43.2 cm.

*Length of internode* (*average*).—1.1 cm between lateral branches and smaller branchlets.

*Strength.*—Strong.

*Pubescence.*—Absent.

Leaves:

*General description.*—Arrangement: Opposite, single. Fragrance: Absent.

*Aspect* (*arrangement on stem*).—Rounded, covered with scale-like leaves.

*Shape.*—Elliptic, scale-like.

*Apex.*—Apiculate.

*Base.*—Cuneate.

*Margin.*—Entire.

*Attachment.*—Sessile (no petioles).

*Appearance.*—Slightly glossy.

*Mature leaf length* (*average*).—0.65 cm.

*Mature leaf width* (*average*).—0.25 cm.

*Quantity per lateral branch* (*average*).—Over 3000 scale-like leaves.

*Pubescence.*—Absent.

*Durability to stresses.*—Very high.

*Venation.*—Veins not visible.

*Color.*—Young foliage (both surfaces): From RHS 143A (Green) to RHS 144A (Yellow-green). Mature foliage (both surfaces): From RHS 137A (Green) to RHS N137A (Green) and RHS N137B (Green).

Inflorescence: No flowers observed to date

Fruit and seed set: No seed set observed

Disease and insect resistance: Not more susceptible to diseases and pests than other *Cupressocyparis leylandii* varieties.

Weather tolerance: Plants of the new *Cupressocyparis leylandii* have been observed to tolerate high temperatures to at least 35° C. and low temperatures to USDA Zone 6.

COMPARISON WITH PARENTAL VARIETY

'Greenpower' is a new and distinct variety of *Cupressocyparis leylandii* having a sturdy, straight upright leader, which creates the cultural advantage of not being necessary to tie the leader to a cane in order to maintain a good upright growth, a very narrow, pyramidal growth habit, and dark green foliage. 'Greenpower' is different from its parent *Cupressocyparis leylandii* because *Cupressocyparis leylandii* has a leader that is not very sturdy or typically straight, creating the need to tie the leader to a cane in order to maintain a good upright growth, has a broader pyramidal growth habit, and has a medium green foliage color.

COMPARISON WITH COMMERCIAL VARIETY

'Greenpower' differs from commercial comparison variety 'Leighton Green' (not patented) in that 'Greenpower' has a sturdy, straight upright leader, which creates the cultural advantage of not being necessary to tie the leader to a cane in order to maintain a good upright growth, a very narrow, pyramidal growth habit, and dark green foliage, while 'Leighton Green' has a leader that is not very sturdy or typically straight, creating the need to tie the leader to a cane in order to maintain a good upright growth, and has a broader pyramidal growth habit.

I claim:

1. A new and unique variety of *Cupressocyparis leylandii* tree named 'Greenpower' as herein shown and described.

* * * * *

UNITED STATES PATENT AND TRADEMARK OFFICE

CERTIFICATE OF CORRECTION

PATENT NO. : PP22,407 P3
APPLICATION NO. : 12/660379
DATED : December 27, 2011
INVENTOR(S) : Cornelis Henricus Maria DeJong It is certified that error appears in the above-identified patent and that said Letters Patent is hereby corrected as shown below:

On the Title Page Item (54)

The title:

"CYPRESS TREE NAMED 'GREEN ROCKET'" should read --CYPRESS TREE NAMED 'GREENPOWER'--

Signed and Sealed this
Sixth Day of March, 2012

David J. Kappos

David J. Kappos
*Director of the United States Patent and Trademark Office*